United States Patent
Jacobs et al.

US005378737A

[11] Patent Number: 5,378,737
[45] Date of Patent: * Jan. 3, 1995

[54] TOOTH RESTORATION COMPOSITION, STRUCTURE AND METHODS

[76] Inventors: Richard Jacobs, 14822 Florwood Ave., Hawthorne, Calif. 90250; Don D. Porteous, 2794 Moraga Dr., Los Angeles, Calif. 90077

[*] Notice: The portion of the term of this patent subsequent to May 19, 2004 has been disclaimed.

[21] Appl. No.: 111,711

[22] Filed: Aug. 25, 1993

Related U.S. Application Data

[63] Continuation of Ser. No. 399,699, Aug. 28, 1989, abandoned, which is a continuation of Ser. No. 739,827, May 31, 1985, abandoned.

[51] Int. Cl.$^6$ .............. A61K 6/08; C08G 18/10; A61C 13/00

[52] U.S. Cl. .............. 523/116; 523/115; 528/59; 528/60; 528/76; 528/77; 433/199.1; 433/201.1; 433/202.1; 433/212.1

[58] Field of Search .............. 523/115, 116; 528/59, 528/60, 76, 77; 433/199.1, 201.1, 202.1, 212.1

[56] References Cited

U.S. PATENT DOCUMENTS

| | | | |
|---|---|---|---|
| 4,281,992 | 8/1981 | Colpitts et al. | 528/66 |
| 4,476,292 | 10/1984 | Ham et al. | 528/60 |
| 4,677,157 | 6/1987 | Jacobs | 524/789 |

*Primary Examiner*—Paul R. Michl
*Assistant Examiner*—LaVonda R. DeWitt
*Attorney, Agent, or Firm*—Louis J. Bachand

[57] ABSTRACT

Method, composition and structure are provided for tooth restorations comprising a urethane polymer having a crystalline polymer phase distributed in a noncrystalline polymer phase by virtue of differential reactivity of the urethane forming reagents.

22 Claims, No Drawings

TOOTH RESTORATION COMPOSITION, STRUCTURE AND METHODS

REFERENCE TO RELATED APPLICATION

This application is a continuation of our co-pending application Ser. No. 07/399,699 filed Aug. 28, 1989, now abandoned, which is in turn a continuation of application Ser. No. 07/739,827 filed May 31, 1985 now abandoned.

TECHNICAL FIELD

This invention has to do with compositions, structures and method for the restoration of natural teeth by application of permanent fillings, crowns, replacements, adhesion of like or dissimilar restorative materials such as amalgam and acrylate resin based restoratives, all based on the discovery of a remarkable urethane polymer system which for the first time enables posterior reconstructions of natural teeth having a toughness as opposed to mere hardness so as to reversibly thermodynamically absorb and return occlusal stresses encountered in mastication, avoiding creep and like maleffects common in other resinous tooth restoratives such as acrylate resins. More particularly, the invention is concerned with methods of forming especially in situ within broad and forgiving clinical parameters a tooth restorative composite which obsoletes previously known resinous restoratives by being readily initially formed in situ during a precure period, e.g by being syringeable into the prepared tooth, condensible on site, adherent to tooth walls, including margin areas, nonadherent to instruments, and easily trimmed for a reasonable period after initial cure, all while affording the uniquely advantageous final properties noted above.

BACKGROUND OF THE INVENTION

Amalgams of silver have long been used in tooth restorations, but they contain mercury and may constitute a health hazard and they are expensive and not esthetic. Moreover, because they are not adherent to the tooth, extra large and undercut preparations in the tooth are required, leaving less of the tooth than might be desirable merely to remove carious conditions.

Acrylate resins have found a market particularly where esthetics are important, e.g. repair of anterior teeth. Transfer of acrylate resins to posterior teeth has been largely unsuccessful, since acrylates are glassy polymers at the temperature of the mouth environment, and as such tend to creep under stress and ultimately fail structurally. In addition, application of acrylate resins is fraught with difficulty, including adhesion of the acrylate to the instruments but not to the tooth structure, causing leakage at the restoration margins, inability to syringe the material into the cavity, inability to condense the positioned resin, hardness without toughness in the cured resin, and hydrophobicity alien to natural structures.

SUMMARY OF THE INVENTION

It is accordingly an object of the invention to provide a novel restorative tooth composition, structure and method. Another object is to provide such a composite wherein natural tooth color is closely matched, the cured resin is indestructible once cured, the morphological structure of the resin is such that the structure is phase segregated into crystalline and amorphous zones defining a truly thermodynamic polymer capable of receiving work energy, delocalizing it and returning it to its surroundings after each mastication cycle so as to avoid destruction inherent in retaining such energy. It is another object to provide such resin which is not clinically critical because its progression is gradual, predictable, and reproducible, because it tolerates mismatching of quantities of reactants, is mixable as a pair of pastes, is so fluid that it can be syringed into place, is non adhesive to dental instruments, requires minimum removal of the natural tooth since it is fluid and self-adheres to the tooth surfaces upon cure, edge margin seals against leakage, can be condensed for perfect interfittment with the tooth preparation, can be swaged and carved to form the approximate occlusal anatomy, and any excess wiped or trimmed away, minimizing grinding time, is low exothermic minimizing injury to tissue, is nonconductive to heat and cold insofar as pulpal response is concerned, equals or exceeds in abrasion resistance silver amalgam, is less stain prone than acrylates, is easily veneered in successive layers increasing clinical options even at widely spaced time periods by virtue of its adhesive and cohesive properties, accepts large quantities of fillers such as vitreous particulate, but does not depend on such for effective performance in a tooth, is free of immune sensitization, oral toxicity, cyto-toxicity and mutagenicity by common tests, is radiopague, and which, in sum, offers a combination of chemical, clinical and performance attributes which make it the material of choice for all dental restorations hereinafter done.

These and other objects to become apparent hereinafter are realized in accordance with the invention by the method of forming a composition useful for restorative tooth structures, including mixing a first side comprising an isocyanato reagent under urethane polymer forming conditions simultaneously with a second side comprising a premix of an hydroxylated tertiary amine reagent and a polyol reagent, shaping for use in a tooth restoration, and reacting to form a polymeric urethane composition useful for restorative tooth structure.

In this and like embodiments, there is included also selecting an isocyanato reagent comprising 4,4'-diphenylmethanediisocyanate; cyclizing the 4,4'-diphenylmethane diisocyanate with itself before mixing for urethane polymer forming reaction; dissolving the cyclized 4,4'-diphenylmethane diisocyanate in noncyclized 4,4'-diphenylmethane diisocyanate before mixing under urethane polymer forming conditions; selecting an isocyanato reagent comprising the polyfunctional isocyanate addition reaction product of an aromatic polyfunctional isocyanate moiety and a hydrophobic organic polyfunctional active hydrogen moiety, e.g. selecting 4,4'-diphenylmethane diisocyanate as the aromatic polyfunctional isocyanate moiety, cyclizing the 4,4'-diphenylmethane diisocyanate and dissolving it in a solution of 4,4'-diphenylmethane diisocyanate in advance of the addition reaction, selecting Isonate 143-L or Mondur CD as the aromatic polyfunctional isocyanate moiety, and selecting hydroxyl-, thiol-, or carboxyl- poly-substituted compounds reactive with isocyanate groups as the hydrophobic organic polyfunctional active hydrogen moiety; selecting polytetraalkyleneoxide ether polyols, polyoxyalkyleneoxide ether polyols, aliphatic diols, or active-hydrogen substituted oligomers and fatty acid esters reactive with isocyanate groups as the hydrophobic organic polyfunctional active hydrogen moiety; selecting active hydrogen substituted silicone, fluorocarbon, fluorochlorocarbon, polytetraalkyleneoxide ether polyols, acrylic, vinyl, butadiene, cis-polyisoprene, polyamide, polyester, vinyl acetate, acrylamide, polyolefin, or Diels-Alder adducts of unsaturated polyester resin oligomers as the hydrophobic organic polyfunctional active hydrogen moiety; also selecting polytetramethyleneoxide ether polyol, D.B castor oil, or hydroxylated glyceryltriricinoleate triester reactive with isocyanate as the hydrophobic organic polyfunctional active hydrogen moiety; reacting the 4,4'-diphenylmethane diisocyanate and the hydroxylated glyceryltriricinoleate triester or like reagent in an inert vessel under high shear conditions at a temperature of about 80° C. for about one hour under a vacuum in excess of one millimeter of mercury; effecting the reaction to an amine equivalency in the product of above about 400; selecting as the polyol reagent a polyol preferentially forming a noncrystalline urethane polymer with the isocyanato reagent under urethane polymer forming conditions; as the polyol an hydroxyl-, thiol-, or carboxyl- poly-substituted oligomer having a molecular weight above about 500 and segregated phase defining reaction with the iscyanato reagent relative to said amine reaction under the same urethane polymer forming conditions; selecting a polyoxyalkylene ether polyol as the polyol reagent; selecting a polyoxyalkylene ether polyol having a molecular weight above about 1000; reacting the polyol with an isocyanato reagent comprising an adduct of liquid 4,4'-diphenylmethanediisocyanate and glyceryltriricinoleate triester to form a noncrystalline urethane polymer; reacting the polyol and isocyanato reagent adduct in admixture with a tertiary amine having a faster rate of reaction with the isocyanato reagent adduct than does the polyol; selecting as the hydroxylated tertiary amine reagent an alkaryl amine, arylamine, mercaptan, alkylene oxide adduct of alkanol amines, alkoxylated or epoxylated ethylenediamines, triazines, amines and hydrazines having hydroxyl, thiol, or carboxyl functionality; selecting as the hydroxylated tertiary amine reagent a compound having the formula:

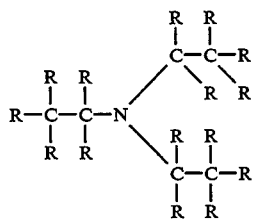

in which at least one R=R1, and each remaining R is R1 or R2, and:
in which:
R1=—OH;  —SH;  —N(CH2CH2)OH2; —N(CH2CH3CH2OH)2;  —N(CH2CHCH3OH)2.
R2=—H; —Me; —Alkyl; —OAlk; —OMe; Halogen, —Aryl;
—Aroyl
selecting as the hydroxylated tertiary amine reagent the compound N'N'N'N'-tetrakis(2-hydroxypropyl) ethylenediamine; selecting as the isocyanato reagent 4,4'-diphenylmethane diisocyanate, and as the polyol reagent polyoxypropylene polyol triol; reacting the isocyanato reagent with the hydroxylated tertiary amine reagent to a crystalline urethane polymer, and with the polyol reagent to an amorphous polymer interdispersed with the crystalline polymer; employing as the first side per 100 parts by weight from 25 to 45 parts of 4,4'-diphenylmethane diisocyanate, from 3 to 8 parts of hydroxylated tertiary amine, glycerylricinoleate triester or polytetramethyleneoxide ether polyol adducted with the 4,4'-diphenylmethane diisocyanate, and the balance a hardening filler; and employing as the second side per 100 parts by weight from from 10 to 30 parts of the polyol, from 10 to 30 parts of the hydroxylated tertiary amine, and the balance zeolite, silica, including silane treated silica, vitreous particulate or mixtures thereof.

The invention further contemplates compositions and structures including the composition useful for restorative tooth structures, comprising a urethane polymer reaction product in the shape of a tooth restoration structure of a first side comprising an isocyanato reagent simultaneously with a second side comprising a premix of an hydroxylated tertiary amine reagent and a polyol reagent.

In this and like embodiments, isocyanato reagent typically comprises 4,4'-diphenylmethanediisocyanate, the isocyanato reagent comprises cyclized 4,4'-diphenylmethane diisocyanate; the isocyanato reagent comprises the cyclized 4,4'-diphenylmethane diisocyanate dissolved in noncyclized 4,4'-diphenylmethane diisocyanate; the isocyanato reagent comprises the polyfunctional isocyanate addition reaction product of an aromatic polyfunctional isocyanate moiety and a hydrophobic organic polyfunctional active hydrogen moiety; the aromatic polyfunctional isocyanate moiety comprises 4,4'-diphenylmethane diisocyanate; the 4,4'-diphenylmethane diisocyanate is cyclized and dissolved in a solution of 4,4'-diphenylmethane diisocyanate; the moiety is Isonate 143-L or Mondur CD; the hydrophobic organic polyfunctional active hydrogen moiety comprises hydroxyl-, thiol-, or carboxyl- poly-substituted compounds reactive with isocyanate groups; the hydrophobic organic polyfunctional active hydrogen moiety comprises polyoxyalkyleneoxide ether polyols, aliphatic diols, or active-hydrogen substituted oligomers and fatty acid esters reactive with isocyanate groups; the hydrophobic organic polyfunctional active hydrogen moiety comprises active hydrogen substituted oligomers selected from silicone, fluorocarbon, fluorochlorocarbon, acrylic, vinyl, butadiene, cis-polyisoprene, polyamide, polyester, vinyl acetate, acrylamide, polyolefin, or Diels-Alder adducts of unsaturated polyester resin oligomers; the hydrophobic organic polyfunctional active hydrogen moiety comprises hydroxylated glyceryltriricinoleate triester reactive with isocyanate; the 4,4'-diphenylmethane diisocyanate and the hydroxylated glyceryltriricinoleate triester compounds are prereacted in a chemically inert vessel under high shear conditions at a temperature of about 80° C. for about one hour under a vacuum in excess of one millimeter of mercury; the prereacted compounds have an amine equivalency in the product of above about 400; the polyol reagent is a polyol preferentially forming a noncrystalline urethane polymer with the isocyanato reagent under urethane polymer forming conditions; the polyol is an hydroxyl-, thiol-, or carboxyl- poly-substituted oligomer having a molecular weight above about 500 and a segregated phase defining reaction with the iscyanato reagent than the amine reaction with the isocyanato reagent under the same urethane polymer forming conditions; the polyol reagent is a polytetraalkyleneoxide ether polyol or polyoxyalkylene ether polyol; the polyol has a molecular weight above about 1000; the urethane polymer is obtained by reaction of the polyol with an isocyanato reagent comprising an adduct of liquid 4,4'-diphenylmethanediisocyanate and polytetramethyleneoxide ether polyol, D.B. castor oil, or glyceryltriricinoleate triester and is a noncrystalline urethane polymer; tertiary amine reagent has a faster rate of reaction with the isocyanato reagent adduct than does the polyol reagent, whereby the urethane polymer comprises a crystalline portion produced by reaction of the amine and the adduct and a noncrystalline portion produced by reaction of the polyol and the adduct, the crystalline portion being dispersed through the noncrystalline portion; the hydroxylated tertiary amine reagent comprises an alkylene oxide adduct of alkanol amines, alkoxylated or epoxylated ethylenediamines, triazines, amines and hydrazines having hydroxyl, thiol, or carboxyl functionality; the hydroxylated tertiary amine reagent a compound has the formula:

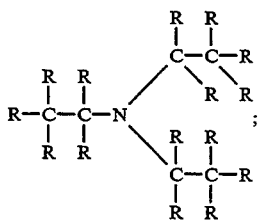

in which at least one R=R1 an deach remaining R is R1 or R2, and:
in which:
R1=—OH; —SH; —N(CH2CH2)OH2; —N(CH2CH3CH2OH)2; —N(CH2CHCH3OH)2.
R2=—H; —Ne; —Alkyl; —OMe; —Cl, —Aryl; —C=O—Aryl the hydroxylated tertiary amine reagent is N'N'N'N'-tetrakis(2-hydroxypropyl) ethylenediamine; the isocyanato reagent is 4,4'-diphenylmethane diisocyanate, and the polyol reagent is polyoxypropylene polyol triol; the urethane polymer obtained by reaction of the isocyanato reagent with the hydroxylated tertiary amine reagent is a crystalline urethane polymer, and the urethane polymer obtained by reaction of the isocyanato reagent with the polyol reagent is an amorphous polymer interdispersed with the crystalline polymer; the polymer comprises per 200 parts by weight from 25 to 45 parts of 4,4'-diphenylmethane diisocyanate, from 3 to 8 parts of glycerylricinoleate triester adducted with the 4,4'-diphenylmethane diisocyanate, from 0 to 30 parts of the polyol, from 10 to 60 parts of the hydroxylated tertiary amine, and the balance a hardening filler; the polymer comprises per 200 parts by weight 35 parts Mondur C, 6 parts glycerylricinoleate triester, 22 parts polyoxypropylene ether polyol, 18 parts ethylenediamine tetra ethoxylate, 10 parts zeolite and the balance vitreous particulate.

In another embodiment the foregoing compositions are combined with a natural tooth, e.g. adhered to a natural tooth substrate; and typically formed in situ against a natural tooth.

In another aspect of the invention there is provided adhesive for adhering material to a natural tooth, the material comprising the foregoing compositions free or not of vitreous filler and bonded to both the natural tooth and to the material.

Still further the invention provides method of adhering a material to a natural tooth, including interposing the foregoing compositions between the material and the tooth, and reacting to the urethane polymer.

In yet another aspect, the invention provides composition useful in the restoration of natural teeth, the composition comprising interdispersed crystalline and noncrystalline portions of a polymer jointly shaped to conform to a natural tooth, in which the polymer crystalline portions are relatively movable under occlusal stress within the noncrystalline polymer portion, whereby the stress is returnably absorbed in the composition in stress-induced failure blocking relation, and the crystalline and noncrystalline portions are formed by reaction of two differentially reactive reagents with a common third reagent; the polymer is a urethane polymer, and the common third reagent is an isocyanato reagent; one of the differentially reactive reagents is a tertiary amine reagent adapted to form a urethane polymer with the isocyanato reagent; the other of the differentially reactive reagents is a polyol adapted to form a urethane polymer with the isocyanato reagent; the one of the differentially reactive reagents is a tertiary amine adapted to form a crystalline urethane polymer with the isocyanato reagent in the presence of the polyol under urethane polymer forming conditions between the polyol and the isocyanato reagent; there is further included a vitreous filler of a kind and in an effective amount to increase the hardness of the composition; and the vitreous filler is borosilicate glass;

In another, broader aspect the invention provides a natural tooth restoration structure, comprising in shaped conformance to a natural tooth, a synthetic organic polymer having generally a glass transition temperature less than the temperature of the mouth environment; e.g. a natural tooth restoration structure in which the polymer is a urethane polymer, or a polyamide polymer; and the polymer is self-adherent to the natural tooth.

In accordance with the invention there is further provided a method of repairing a natural tooth structure, including removing carious areas of the tooth, and applying the reactive precursors of the foregoing compositions; e.g. the composition precursors are applied as a mixture of first and second reagents differentially reactive with a common third reagent to form the crystalline and noncrystalline polymer portions, whereby the composition is partially crystalline, typically and preferably, the noncrystalline polymer portion has a glass transition temperature below the temperature of the mouth environment, and the crystalline portion is discontinuously distributed within the noncrystalline portion; and there is further included condensing the precursors against the natural tooth in advance of full polymerization of the polymer, and/or building the composition in separate veneer layers of the precursors.

In another embodiment there is provided a method of preparing an isocyanato reagent precursor for a urethane polymer, including adducting a polyisocyanate with a hydrophobic fatty acid reagent having hydroxyl functionality in advance of reacting the reagent with an active hydrogen compound to form a urethane polymer, e.g. selecting 4,4'-diphenylmethane diisocyanate as the polyisocyanate, and glyceryltriricinoleate ester as the fatty acid reagent, or the oligomers listed above as the fatty acid reagent; and the compositions prepared by these methods.

The invention further provides method of preparing a tertiary amine reagent precursor for a urethane polymer, including adducting hydroxyl functionality onto a tertiary amine reagent in advance of reacting the reagent with an isocyanato reagent to form a urethane polymer. In addition the invention provides method of enhancing the malleability of a urethane polymer composition to be shaped against a natural tooth, including incorporating above about 5% by weight up to about 15% by weight zeolite, such as sodiumaluminosilicate at 2 to 10 angstroms or smaller or larger, in the composition. Further method is provided of enhancing the appearance and effectiveness of a dental composite in the mouth by superimposing a surface layer of the novel compositions hereof on the dental composite, which is non staining to common foods and more abrasion resistant, whereby the composite is prevented from degradation.

Preferred Modes

The ensuing detailed description of a preferred embodiment of the invention tooth restorative, its precursors and products has reference to the properties of the components during their various stages toward achieving the final composite state: during (1) storage of Part A (sometimes first part or side) and Part B (sometimes second part or side) in their respective containers; (2) the initial mixture of the components; (3) the malleable phase; (4) the final composite state.

In preparation, the first step is the synthesis of the Part A and Part B components. For the Part A component: 4,4'-diphenylmethane diisocyanate (sometimes MDI) is converted through the Wittig reaction into a cyclized structure.

This cyclized structure is then dissolved in a solution of MDI to produce a storage-stable liquid form called liquid MDI having an overall isocyanate functionality of 2.1 to 2.2. Pure 4,4'-diphenylmethane diisocyanate could have been selected to produce the prepolymer, but this special form was used as the reactive isocyanate in order to produce a more storage-stable solution (stable towards freezing during storage). This liquid MDI form is commercially available from Upjohn Company as Isonate 143-L or from Mobay Chemical as Mondur CD.

A quasi prepolymer is synthesized from the addition reaction of liquid MDI (Mondur CD) and preferably gylceryltriricinoleate triester (sometimes GTR). Placed into the reaction solution was Kimble T-3000 ground barium borosilicate glass of a nominal 10 micron diameter particle size along with fumed silica of a 0.04 micron size. This composition was placed in an inert reaction vessel which was capable of heating the reaction mixture, controlling its reaction temperature, high-shear mixing, and a vacuum exceeding one millimeter. The ingredients were high-shear mixed and heated to 80–85 degrees centigrade for one hour. During this time, a vacuum was pulled on the mixture in excess of one millimeter of mercury. The amine equivalent was measured and the synthesized mixture packaged in metal squeeze tube containers which acted as a non-permeable barrier to moisture. The ratio of the ingredients is such that the overall theoretical amine equivalent weight of the prepolymer mixture was 451.5. The actual amine equivalent weights achieved ranged from 460 to 465. The barium borosilicate glass and fumed silica were selected from the available fillers for the following properties: providing a non-basic residual which would otherwise produce an unstable prepolymer mixture (tending to form isocyanurate reaction products), radiopaque properties, fineness of particle size and acceptable color and translucency. The barium The Part A (prepolymer) component utilizes the extremely hydrophobic glyceryltriricinoleate triester hydroxyl-functional compound, e.g. a refined castor oil. This compound was selected on the basis that its hydrophobic character stabilized the prepolymer towards reaction with extraneous moisture contamination, during the following stages of its potential exposure to moisture: preparation of the prepolymer, packaging of the Part A component, storage of the Part A component in metal squeeze tube containers, mixing the Part A with the Part B component on the mix pad, introduction of the mixture to the oral cavity, residence of the polymerizing mixture in the prepared cavity and residence of the restoration in-vivo. Other hydroxyl-functional compounds which could have been selected to achieve this hydrophobic property include such compounds as polyoxytetramethyleneoxide ether polyols, polyoxypropylene either polyols, cyclohexanedimethylol, hexanediol, dipropylene glycol, tripropylene glycol, propylene glycol, ethylene glycol, diethyleneglycol, triethylene glycol, 1,3-butanediol, butanediol, propargyl alcohol, butyne diol, and the family of di- and tri-functional monomers or polyols, as well as silicone-, flurocarbon-, fluorochlorocarbon-, acrylic-, vinyl-, butadiene-, cis-polyisoprene-, polyamide-, polyimide-, Diels-Alder adducts of unsaturated polyester resin-, polyester resins, vinyl acetate-, acrylamide-, polyolefin-, and any combination of the above oligomers modified to have active-hydrogen functionality. Carboxylic acid-functional-, thiol functional- and other active-hydrogen-functional oligomers or monomers can also be selected to be reacted with the isocyanate to form the prepolymer used as the isocyanato reagent.

The Part B (polyol reagent) is preferably partially composed of a high molecular weight polyol oligomer, e.g. a 500 to 1000 up to 6000 molecular weight and higher liquid tri-functional polyoxypropylene ether polyol having some ethylene oxide capping to give secondary functionality. Any modification of the foregoing hydrophobic compounds may be selected as long as the reactivity of the polyol component its reactivity is slower than the tertiary amine coreactant or such as to define a phase segregated polymer relative to that defined by the amine reaction with isocyanate during formation of the polymer, so that the polyol forms essentially (i.e. thermodynamically) random structure by virtue having little ability to crystallize, or organize its structure, and it has the correct solubility to phase-segregate from the crystalline amine isocyanate adduct phase and to thereby form multi-phase matrix structures. It addition the polyol should have sufficient functionality to crosslink with the crystalline "zones" even if the clinician should mix the Part A and Part B components off-ratio enough to cause the cross-link density to be reduced, should have some tendency to cyclize or helicize, or form polymeric strands which are capable of being elongated when the multi-phase structure is stressed by an outside force, and most importantly, have the ability to return to its random or amorphous structure once the external force, e.g. from mastication, is relieved.

In combination with the just-described polyol is a hydroxyl-reactive amine compound capable of forming highly crystallized and ordered structures upon reaction with the isocyanate functionality in the Part A component. The amine reagent preferably is a somewhat ordered structure containing tertiary amine groups. While not wishing to be bound to any particular theory of operation, it is theorized that the tertiary amino groups of amine reagent herein, having a free-electron pair, orients that electron pair with some other moiety in the polymer solution (in its pre-polymerized form) to resist unwanted melting during grinding in small less than one gram aliquots, whereby structures of adducts can be visualized which show a high crystalline and oriented structure capable of withstanding many kilocalories of input heat during a grinding process such as during the finishing of a restoration, and the highly organized nature of these crystalline zones can be supposed to have sufficient intramolecular forces to remain intact, while only amorphous zones would be unsupportive at their interstices and consequently "ablate" during the grinding process. In general it is significant that only the tertiary amino groups, not having reactive hydrogen functionality on the amino groups themselves in order to withstand instant reactivity, function herein as the amine reagent. In addition, the tertiary amino groups must have hydroxyl functionality adducted. The best means of adducting is to use ethylene oxide or propylene oxide so that only one ethylene or one propylene is adducted to each active hydrogen of the tertiary amino group. Illustrative amine reagents herein are: triethanol amine; tripropanol amine; combinations of diethanol-monopropanol amine, etc.; ethylenediamine tetra ethyoxylate; ethylenediamine tetrapropoxylate; ethoxylated and propoxylated 1,3,5-triazines, or other triazine isomers; cyclic combinations of ethylenediamine, hydrazine, amines which are ethoxylated, propoxylated or epoxidized in any form which leaves hydroxyl, or thiol functionality.

The Part B side also contains a zeolite, such as a sodiumaluminosilicate zeolite structure, e.g. capable of containing at least one molecule of water within its clathrate structure. It has been found that levels of zeolite substantially exceeding 5 percent up to as much as 85% substantially improve the malleable properties of the invention composition, and substantially improve the physical properties of the restorative for condensing, swaging, articulating, carving and grinding. Moreover, the invention composition is substantially improved in its resistance to side reactions with moisture, and maintains an "ablative" characteristic which is otherwise not present when this zeolite is not admixed. Again, it is theorized that the zeolite is acting synergistically with the amine reagent in producing the required "through-cure" and "ablative" properties so significantly present in the invention composition.

A radiopaqued glass is also incorporated into the Part B side in certain preferred examples. This blend was prepared using the same reaction vessel described above. The ingredients were high-shear mixed in the vessel, heated to 105-110 degrees Centigrade in order to ensure that all water was removed from the mixture. The filled polyol component was packaged in its own separate metal squeeze tube container for storage.

The composition of the Part A and Part B pastes when extruded onto the mix pad, then upon being mixed and during the syringable stage is as follows: Both the Part A and Part B components desirably produce the correct viscosity pastes for extruding out of a number 10 orifice from a metal squeeze tube at nearly equal and controlled diameters. By extruding equal length lines of pastes on a moisture-resistant mixing pad, the volume ratios are maintained at roughly 1.00 to 1.00. The achievement of control of the mix ratios is very important for maintenance of the stoichiometry of the reactive components and for achieving maximum molecular weight polymers in the composite matrix. The composition is preferably built upon, e.g. the trifunctional ricinoleate, trifunctional high-molecular weight oligomer, and the tetra-functional N,N,N,N-tetrakis(2-hydroxyethyl or propyl)ethylenediamine in order to achieve an extremely high level of off-ratio or poor mixing forgiveness encountered in lax clinical use of the product. The mixed ingredients have filler levels and matrix oligomer viscosities which are selected for being syringed into narrow-channeled cavities.

In the malleable phase, the Part A component, composed of 4,4'-diphenylmethane diisocyanate and 4,4'-diphenylmethane diisocyanate-glyceryltriricinoleate triester prepolymer, reacts first with the active hydrogen groups (hydroxyls) on the tertiary amine hard segment crosslinkers of the Part B component. The reaction of 4,4'-diphenylmethane diisocyanate is fast with the tertiary amine in comparison with the reactivites of the 4,4'-diphenylmethane diisocyanate prepolymers and the polyol reagent moieties. The fast reaction produces crystalline hard segments which align into morphological phases within the unreacted or partially-reacted polyol and 4,4'-diphenylmethane diisocyanate prepolymer phases. This crystalline composition within the liquid amorphous phases produces the malleable consistency of the mixture which occurs between two and four minutes after the start of mixing. Condensing the polymer at this point does not fracture the interstices because the amorphous phases have not yet cross linked with the crystalline phases. The forces of condensation merely cause laminar flow and alignment of the hard segments in the liquid soft segment medium. Polymerization continues until the soft segments crosslink the various hard segments and the polymer becomes intractable. At that point, the reversible thermodynamic feature of the invention is apparent as further deformation causes the polymer to uptake the external work of deformation and return it to the surroundings again when external deformation forces are relieved.

The fully-cured restorative is a multi-phase matrix where the crystalline zones (phases) of the matrix are contained within the amorphous zones. The crystalline zones are tied to the amorphous zones through the prepolymer portion of the Part A component. The multi-phase matrix has the capability of uptaking external forces (e.g., from mastication) through thermodynamic ordering of the amorphous zones. The polyol has the capability of uptaking these stresses because the pendant methyl groups on the polyoxypropylene ether polyol provide barriers to rotation which can be easily overcome by the forces of deformation to produce a $\beta$-pleated sheet conformer if the need for uptaking work energy in the form of ordering (negative entropy) is required. Moreover, the pendant methyl groups provide only a low resistance to barriers of rotation allowing the number of possible structures to be high (high randomness) when external forces are relieved. This return of the work energy in the form of entropy prevents incipient destruction of the polymer by minimizing any retained work (low hysteresis).

It has been found that the invention compositions have natural adhesive affinity to conventionally etched enamel structure.

Clinical Properties

The paste-like components are easily extruded at equal lengths on a mix pad. The physical properties can depend upon the mix ratio accuracy and the mix intimacy between the Part A and Part B pastes. Tests have shown that level properties are maintained when the mix ratios have been purposely varied by approximately 2-times excess Part A and, conversely, 2-times excess Part B. In theory, the optimum properties are achieved when a 1:1 ratio by volume of Part A and Part B is used.

The components are mixed with a dental spatula and form a flowable paste composition. Back-filling into a syringe allows easy introduction into a prepared cavity. The viscosity is low enough that the composition can be introduced to the deepest portion of the cavity and injected as the syringe is drawn to the surface. It has been shown that nearly perfect adaption to the cavity walls is achieved. By comparison, acrylate composites are only difficultly placed into large cavity preparations mainly due to their pasty consistency and their inherent stickiness to placement instruments.

During the length of time typically required to complete this filling process, the mixture has achieved a consistency where it can be swaged to conform closely to the required anatomy. For example, a probe or similarly shaped instrument can be used to shape the occlusal anatomy for Class 1 restorations. This technique can reduce the grinding time typically required achieve articulation.

The composition achieves the consistency of silver amalgam approximately four minutes after the start of mixing. This offers the additional convenience of allowing the composition to be condensed against the matrix band in Class 2 restorations. Nearly perfect interproximal adaptation can be achieved using this technique. This process also ensures marginal integrity and a perfect seal against invasive fluids and bacteria.

As noted above, during the process of condensing, the invention composition is not fractured, but it flows and knits with itself until further force from condensing will no longer create any flow or deformation. The composition adheres to etched enamel and dentin surfaces with each application of pressure from a plugging instrument. The plugging instrument neatly pulls away from the composite without stickiness. The polymerization reaction is gradual and predictable producing only a slight exotherm. The concomitant shrinkage at the bond line is almost insignificant and results in little or no residual stressing on the bond line after polymerization is complete. The limited shrinkage that does occur takes place on the non-contact surfaces.

Occulusal articulation can simply be achieved for Class 2 restorations using the following procedure: The prepared cavity is filled to a slight excess. After condensation, the patient then bites down on a thin plastic release film which causes the material to flow and to achieve the approximate occlusal anatomy. The excess flow has a hard rubber consistency and is easily trimmed off with a sharp-edged scraper or scalpel. Further grinding is not typically required but can be achieved with a fluted flame-tipped burr without galling. The composition properties allow a period for grinding from 6 to 20 minutes after the start of the procedure. Grinding does not cause shattering as can occur with acrylate composites.

The composition continues to harden at a controlled rate until nearly full properties are achieved after 2 hours. Full properties are achieved after 24 hours.

In-Vivo Properties

While long term testing results are not yet available, it is anticipated, because of the chemical nature and physical structure of the invention composition is likely to have substantial abrasion resistance in the mouth. Laboratory tests using accelerated methods show the composition to be superior to 3M's P10 acrylate-glass composite, and roughly equivalent to Phasealloy amalgam. The elastomeric properties appear to provide resistance against marginal breakdown from the mechanical forces of occlusion and from expansive and contractive forces from hot and cold liquids.

A considerable advantage of the present composition is that re-veneering is possible even after a long period from the first installation; the adhesion of the composition to itself allows this to be accomplished.

Restorations with the composition are non-toxic and have been tested for immune sensitization, oral toxicity, cyto toxicity and for mutagenicity (by the Ames Test). All result are negative. In addition the composition provides a resistance to thermal conductivity thus reducing pulpal sensitivity to hot and cold liquids, is esthetically attractive and nearly approximates the appearance of enamel in the posterior areas. It has less of a tendency to stain than acrylate composites.

EXAMPLES

Example 1

| Part A: | |
|---|---|
| Mondur CD | 21.3 |
| D.B. Castor Oil | 3.6 |
| Silaned Quartz | 75.0 |
| PART B: | |
| 6000 Mol Wt. Polyether Triol | 18.0 |
| N,N,N,N-tetrakis(2-hydroxypropyl) ethylenediamine | 9.0 |
| Sodium Alinumunosilicate Zeolite Powder | 10.0 |
| Silaned Quartz | 57.8 |
| Titanium Dioxide in Polyether Polyol, 50% | 5.0 |
| Dibutoxytin Disulfide | 0.2 |

The composition reached a stage at approximately one minute after mixing when it was firm, non-tacky and easily placeable. It was condensible at this stage and gradually increased in hardness somewhat like amalgam so that continued compaction was achieved until 3½ to 4 minutes when it was easily carvable and shapeable. After 5 minutes, it was at the hardness to be grindable. The hardness properties continued to build gradually to form a very hard elastomer after one hour when it reached nearly full properties. Full hardness properties were reached after 24 hours.

Control

3M's P10 restorative was a soft, gummy mixture for the first minute after the start of mixing. Between the period of one and 2½ minutes the material was tacky and difficult to place. Placement could not be achieved with compaction except within the very narrow time-frame spanning approximately 5 seconds. During this 5 second period the resin gelled to form a weak soft composite. Compaction during and after gelation probably ran a high risk of fracturing the matrix. This evaluation is made on the basis that the material was weak and spongy just at the time of gelation until 30 seconds afterwards. Carving and grinding caused chipping when attempted within the first 2 minutes after gelation. The resin was hard but somewhat weak at this point.

To evaluate the invention composition, a second molar human tooth was ground flat on the occlusal surface. A circular cross-section was developed by grinding the mesial, distal, buccal and lingual surfaces to a diameter of 7.5±0.5 mm. The ground tooth was then cast into a support block using a hard epoxy casting resin forming a cube which was 20 mm on each side. Then an aluminum block was machined into a cube having a face of 20 mm×20 mm and being 10 mm thick. A hole was drilled through the face of the aluminum block having a diameter of 7 mm. By placing the aluminum block on top of the cast block containing the cast tooth, a test cavity was developed with the hole overlapping the exposed cementum surface. A jig was then designed to firmly hold the epoxy and aluminum blocks in the jaws of a tensile tester.

The cementum surface was then etched using 35% phosphoric acid for 120 seconds, washed clean with distilled water and blown dry using air. With the test cavity in place (out of the tester jaws), test material was mixed and compacted into the cavity using the clinical application and compaction procedures prescribed by the particular manufacturer. The bonded blocks were allowed to remain undisturbed for a period of 24 hours. The tensile mode of the tester was then used to measure the resistance to delamination of the interface between the cementum and the restorative material using a straining rate of 0.33 mm/sec. The results of the adhesion tests are shown in Table 1.

TABLE 1

| Adhesion of Test Composite And Controls to Cementum: | |
|---|---|
| Test Material | Adhesion in the tensile mode, g/cm sq |
| Phasealloy amalgam | 0 |
| " | 0 |
| P10 Composite, no post-gel compaction | 70.3 |
| P10 Composite, no post-gel compaction | 421.8 |
| P10 Composite, post-gel compaction | 6467. |
| P10 Composite, post-gel compaction | 1687. |
| Example 1 | 7311. |
| Example 1 | 5765. |

P10 restorative was found to have highly variable bonding strengths depending upon the compaction technique. When compaction was accomplished prior to gelation, then the average of two duplicate tests was 211 g/dm sq. When compaction was continued during and after gelation, two duplicate tests gave average tensile strengths of 4077 g/cm sq. Our tests show that P10 acrylic composite has virtually no adhesion to etched-cementum without achieving compaction. The most obvious deficiency is that P10 (and all acrylics) resist being compacted due to an inherent lack of a continuous, non-accelerating build-up of hardness during polymerization.

Two duplicate tests were using the example material. The urethane was mixed on the pad for 30 seconds, and a compaction instrument was used to deliver the urethane to test cavity within 1 minute. Loading and compaction was continued until 3 minutes had elapsed. The composite was carved smooth after 5 minutes to simulate actual clinical methods. The composite was allowed to remain undisturbed for 4 hours before being tested. The average tensile strength was 6538 g/cm sq.

The Shore Durometer was used to determine the hardness of the urethane and other materials. The results are shown in Table 2.

TABLE 2

| Shore Durometer Hardness | | |
|---|---|---|
| | Shore D Hardness | |
| Sample Type | Initial | 10 second dwell |
| Example 1 | 91 | 90 |
| | 92 | 91 |
| | 93 | 92 |
| | 90 | 89 |
| | 89 | 87 |
| P10 Acrylic composite | 99 | 98 |
| | 98 | 98 |
| | 99 | 99 |
| | 98 | 98 |
| | 99 | 99 |
| Amalgam | 97 | 97 |
| | 99 | 99 |
| | 98 | 98 |
| | 97 | 97 |
| | 99 | 99 |
| | 99 | 99 |
| Human tooth enamel, 2nd molar exterior | 100 | 100 |
| Human tooth enamel, 2nd molar interior | 100 | 100 |
| Human tooth dentin, 2nd molar | 100 | 100 |

Hardness has historically been considered one of the key parameters for judging the applicability of a prospective composite for posterior applications. Because enamel is the hardest of all naturally occurring biological materials, there apparently has been an a-priori requirement for occlusal restoratives to have enamel hardness in order to replicate the natural mastication processes. It is our feeling that a restorative material is not necessarily as hard as enamel in order to provide mastication and have abrasion resistance. The invention composition has the hardness of a very hard elastomer and for all intents and purposes is hard enough to resist most indentation forces.

Example 2

Example 1 was repeated using ground glass rather than quartz silica to improve color. This sample had a more natural tooth appearance.

| Formula Materials | Eq Wt | Eq | Weight |
|---|---|---|---|
| Mondur CD, Mobay Chemical Co. | 144 | .244 | 35.2 |
| D.B. Castor Oil, Caschem | 315 | .019 | 5.9 |
| Corning 7740 Ground Glass | — | — | 58.8 |
| Total Part A | 443 | .225 | 99.9 |
| Multranol 3901 (polyol) | 2000 | .011 | 22.0 |
| Quadrol, BASF Wyandotte (tert. amine) | 73 | .246 | 18.0 |
| MS4A Powder (zeolite) | — | — | 10.0 |
| Corning 7740 Ground Glass | — | — | 50.0 |

The example 2 composition was evaluated by a dentist. The product was introduced to him as a novel composite. He evaluated the mixing and setting properties vis-a-vis 3M's P30. After looking at the composite being mixed, he immediately picked up a Centrix syringe, back-loaded it and found that it could be syringed into a prepared cavity on a typodont. He was favorably impressed by this syringable characteristic along with the property of controlled reactivity. He concurred that the material was condensible and that it knit to itself as he condensed it with an amalgam carrier. He then selected a flame-tipped, 12-fluted burr and ground the composite and the occlusal anatomy without galling the burr.

We then showed him a sample of an extracted second molar which had been bonded on one side with P10 and on the other side with Example 2 composite. No bonding preparation was made with either composite. He found, just as we had in previous trials, that the P10 could be flicked off the cervical surface with the thumbnail whereas the Example 2 composite remained intact upon attempting to be debonded, even with a sharp-edged knife.

EXAMPLE 3

Another urethane composite was made with the following composition:

|  | Parts by weight |
|---|---|
| Part A: | |
| Liquidfied diphenylmethane diisocyanate | 35.2 |
| Gyceryltriricinoleate | 5.9 |
| Amorphous glass (10 micron average particle size) | 58.8 |
| Fumed silica, untreated | 1.5 |
| Part B | |
| 6000 MW polyoxypropyleneoxide polyol triol | 20.0 |
| ethylenediamine tetrapropoxylate | 14.0 |
| sodiumaluminosilicate, 4 angstrom pore size | 16.0 |
| amorphous glass, 10 micron average particle size | 50.0 |

This system gave reactivity properties which suggested the following clinical parameters:

| Clincal Parameters for class 1 restorations | Time required for each step | Total elapsed time |
|---|---|---|
| Mixing time | 0.5 minutes | 0.5 minutes |
| Back-filling syringe | 0.5 minutes | 1.0 minutes |
| Injecting composite into cavity | 1.5 minutes | 2.5 minutes |
| Waiting for cohesive body to build | 1.0 minutes | 3.5 minutes |
| Condensing the composite | 1.0 minutes | 4.5 minutes |
| Taking the bite articulation | 0.5 minutes | 5.0 minutes |
| Trimming off the excess composite | 1.0 minutes | 6.0 minutes |
| Grinding the occlusion to final articulation | 2.0 minutes | 8.0 minutes |

An important attribute of the urethane composites of the invention is that they can be mixed with variations encountered in actual clinical procedures yet give consistent and optimum restorative properties. One of the major conditions which can be varied in clinical procedures is the mix ratio. To test the mix ratio variability, several 5 inch lines of Part A and Part B were laid out on a mixing pad. Five replicate tests gave weight ratios of Part A and Part B as follows: 1.4/1.3 grams, 1.2/0.8 grams; 1.0/1.0 grams; 1.1/1.2 grams; 1.0/1.0 grams. These ratio variations were translated to the following stoichiometric indices for the composite: 118, 163, 109, 100, and 109. These stoichiometric indices relate to the optimum theoretical properties of the composite. A stoichiometry of approximately 120 is considered to be the optimum stoichiometry for this composite system. Based upon these variations, it was considered that the composite should have reliable and level properties with variations in mixing almost to a 1.5:1 excess of Part A over Part B, and the converse—almost a 1.5:1 excess of Part B over Part A. The hardness properties of composite were tested at a later date and showed that the hardness dis not vary significantly with ratios at a stoichiometry ranging from 70 to 160.

Adding all of these extruded lines together in the above ratio tests gave a urethane composite ratio of 6.9 grams of Part A to 6.3 grams of Part B which relates to a 118 index, close to the theoretical optimum. These lines together gave a total weight of 13.2 grams of system. Upon mixing, the system had the following reaction properties at 70 degrees F. ambient conditions: A syringing time of up to 2 minutes, a condensing period of between 2 and 4.5 minutes, an articulation bite time of between 4.5 and 5.5 minutes, a carving time of between 5 and 7 minutes, and a grinding time of between 7 and 20 minutes. The urethane continued to harden so that a hardness of 89 Shore D was achieved after 24 hours. The hardness did not change from 89 Shore D after 7 days on the benchtop at ambient conditions. The urethane had an excellent appearance and it had looked somewhat like tooth structure, although it was whiter and more opaque. The urethane was used to replace one class 1 amalgram restoration, a right maxillary second molar on experimental patient Number 1. The amalgram was removed leaving a very slight amount at the pulp base. The debris was thoroughly removed and the cavity dried. A calcium hydroxide base was applied and allowed to cure. The cavity was dried thoroughly. The urethane was mixed and back-loaded into a discardable-type syringe. The tapered tip was cut off slightly to provide approximately a one-sixteenth inch diameter opening in the syringe orifice. The urethane was injected into the cavity and an excess applied. The urethane was applied at approximately 2 minutes after mixing.

We claim:

1. Composition for restorative tooth structures, comprising a urethane polymer reaction product of a first side and a second side condensed in the shape of tooth restoration structure against a natural tooth, said first side comprising an aromatic isocyanato reagent reacted simultaneously with each reagent of said second side, said second side comprising a premix of an hydroxylated tertiary amine reagent and another polyol reagent, said premix reagents being differentially reactive with said isocyanato reagent.

2. The composition of claim 1 formed in situ against natural tooth structure.

3. A laminate of the composition claimed in claim 1 and an acrylic dental composite on a natural tooth.

4. Method of preventing staining, wear, cracking or like degradation of acrylic dental composites which includes overcoating said composite with a urethane polymer reaction product claimed in claim 1 in areas to be protected from degradation.

5. The overcoated acrylic dental composite produced by the method claimed in claim 4.

6. Composition for restorative tooth structures, comprising a urethane polymer reaction product of a first side and a second side condensed and adhered in the shape of a tooth restoration structure against a natural tooth, said first side comprising an aromatic isocyanato reagent reacted simultaneously with said second side comprising a premix of an hydroxylated tertiary amine reagent and another polyol reagent, said premix reagents being differentially reactive with said isocyanato reagent.

7. Method of adhering a material to a natural tooth, including interposing the composition of claim 6 between said material and said tooth, and reacting to said urethane polymer.

8. Adhesive for adhering material to a natural tooth, said adhesive being free of vitreous filler and comprising a urethane polymer reaction product of a first side and a second side, said first side comprising an aromatic isocyanato reagent reacted under urethane polymer forming conditions simultaneously with each reagent of said second side comprising hydroxylated tertiary amine reagent and another polyol, and bonded to both said natural tooth and to said material.

9. Natural tooth restoration structure of a composition comprising interdispersed crystalline and noncrystalline portions of a urethane polymer formed by reaction of an aromatic isocyanato reagent under urethane polymer forming conditions simultaneously with an hydroxylated tertiary amine and another polyol which are differentially reactive therewith to form said crystalline and noncrystalline portions interdispersed and shaped into a structure against a natural tooth in adhering relation to conform to said natural tooth.

10. Structure according to claim 9, in which said polymer crystalline portions are relatively movable under occlusal stress within said noncrystalline polymer portion, whereby said stress is returnably absorbed in said composition in stress-induced failure blocking relation.

11. Structure according to claim 10, in which said crystalline and noncrystalline portions are formed by reaction of two differentially reactive reagents with a common third reagent.

12. Structure according to claim 11, in which one of said differentially reactive reagents is a tertiary amine reagent adapted to form a urethane polymer with said isocyanato reagent and comprising an alkaryl amine, arylamine, mercaptan, alkylene oxide adduct of alkanol amines, alkoxylated or epoxylated ethylenediamines, triazines, amines and hydrazines having hydroxyl, thiol, or carboxyl functionality.

13. Structure according to claim 12, in which one of said differentially reactive reagents is a tertiary amine reagent adapted to form a urethane polymer with said isocyanato reagent an comprising N'N'N'N'-tetrakis (2-hydroxyethyl or propyl) ethylene diamine.

14. Structure according to claim 13, in which the other of said differentially reactive reagents is a polyol or tertiary amine other than said tertiary amine reagent and adapted to form a urethane polymer with said isocyanato reagent.

15. Structure according to claim 13, in which the one of said differentially reactive reagents is a tertiary amine adapted to form a crystalline urethane polymer with said isocyanato reagent in the presence of said polyol under urethane polymer forming conditions between said polyol and said isocyanato reagent.

16. Structure according to claim 9, including also a vitreous filler of a kind and in an effective amount to increase the hardness of said composition.

17. Structure according to claim 16, in which said vitreous filler is a borosilicate glass.

18. The method of repairing a natural tooth structure, including removing carious areas of the tooth, and thereafter applying to said areas said reactive precursors of the composition of claim 1 as a mixture of first and second reagents differentially reactive with a common third reagent to form said crystalline and noncrystalline polymer portions, whereby said composition is partially crystalline.

19. The method according to claim 18, in which said crystalline portion is discontinuously distributed within said noncrystalline portion.

20. The method according to claim 18, including also condensing said precursors against said natural tooth in advance of full polymerization of said polymer.

21. The method according to claim 18, including also building said composition in separate veneer layers of said precursors.

22. Method of enhancing the appearance and effectiveness of an acrylic dental composite, including superimposing onto exposed portions of said composite in the mouth, a surface layer comprising a urethane polymer reaction product formed on said acrylic dental composite on a natural tooth, said reaction product being formed by reaction of a first side comprising an isocyanato reagent simultaneously with a second side comprising a premix of an hydroxylated tertiary amine reagent and another polyol reagent, said premix reagents being differentially reactive with said isocyanato reagent in adhering relation.

* * * * *